United States Patent [19]

Armstrong et al.

[11] Patent Number: 5,458,678
[45] Date of Patent: Oct. 17, 1995

[54] ALKALINE EARTH METAL SALTS, TRANSITION METAL SALTS AND TRANSITION METAL COMPLEXES OF KETOCARBOXYLIC ACIDS AS CORROSION INHIBITORS

[75] Inventors: William P. Armstrong, Belfast, Northern Ireland; Adalbert Braig, Binzen; Markus Frey, Marly; Andreas Kramer, Düdingen, both of Switzerland

[73] Assignee: Ciba-Geigy Corporation, Ardsley, N.Y.

[21] Appl. No.: 222,766

[22] Filed: Apr. 4, 1994

[30] Foreign Application Priority Data

Apr. 7, 1993 [CH] Switzerland .................. 1059/93

[51] Int. Cl.$^6$ .................. C09D 5/00; C07C 51/00
[52] U.S. Cl. .................. 106/14.41; 106/14.13; 106/14.15; 106/14.42; 106/14.43; 106/14.44; 252/388; 252/394; 252/396; 427/385.5; 427/386; 427/388.1; 427/388.4; 562/465; 562/471; 562/496
[58] Field of Search .................. 106/14.13, 14.15, 106/14.41, 14.42, 14.44, 14.43; 562/465, 471, 496; 252/388, 394, 396; 427/385.5, 386, 388.1, 388.4; 524/394, 395, 396, 398, 400

[56] References Cited

U.S. PATENT DOCUMENTS

| | | | |
|---|---|---|---|
| 3,382,081 | 5/1968 | Cutter et al. | 106/14.05 |
| 3,876,800 | 4/1975 | Krausz et al. | 424/317 |
| 4,909,987 | 3/1990 | Penninger et al. | 422/17 |
| 5,250,325 | 10/1993 | Philips et al. | 106/14.42 |
| 5,277,709 | 1/1994 | Armstrong et al. | 106/14.42 |

FOREIGN PATENT DOCUMENTS

| | | |
|---|---|---|
| 0144663 | 6/1985 | European Pat. Off. . |
| 0300325 | 1/1989 | European Pat. Off. . |
| 0412933 | 2/1991 | European Pat. Off. . |
| 0496555 | 7/1992 | European Pat. Off. . |
| 2021445 | 12/1970 | Germany . |

OTHER PUBLICATIONS

Houben–Weyl Methoden der Organischen Chemie (1952) 381–382 (no month).
Houben–Weyl Methoden der Organischen Chemie (1985) 398–399 (no month).

*Primary Examiner*—Anthony Green
*Attorney, Agent, or Firm*—Luther A. R. Hall; Michele A. Kovaleski

[57] ABSTRACT

There are described novel alkaline earth metal salts, transition metal salts and transition metal complexes of compounds of the formula I

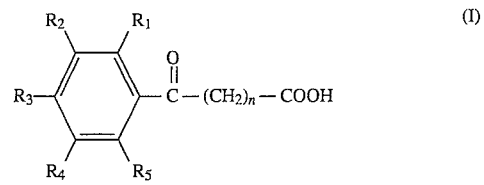

in which $R_1$, $R_2$, $R_3$, $R_4$ and $R_5$ are, independently of one another, hydrogen, halogen, nitro, cyano, $CF_3$, $C_1$–$C_{15}$alkyl, $C_5$–$C_{12}$cycloalkyl, $C_2$–$C_{15}$alkenyl, $C_1$–$C_{12}$haloalkyl, $C_1$–$C_{12}$alkoxy, $C_1$–$C_{12}$alkylthio, $C_6$–$C_{10}$aryl which is unsubstituted or substituted by $C_1$–$C_4$alkyl; $C_6$–$C_{10}$aryloxy which is unsubstituted or substituted by $C_1$–$C_4$alkyl; $C_7$–$C_{12}$arylalkyl which is unsubstituted or substituted on the aryl radical by from 1 to 3 $C_1$–$C_4$alkyl groups; —$CO_2R_6$, —$COR_6$ or

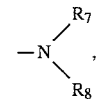

where at least one of the radicals $R_1$ to $R_5$ is hydrogen, halogen or $C_1$–$C_{15}$alkyl, in addition the radicals $R_1$ and $R_2$, $R_2$ and $R_3$, $R_3$ and $R_4$ or $R_4$ and $R_5$ form, together with the carbon atoms to which they are bound, a benzo or cyclohexenyl ring, $R_6$ is $C_1$–$C_{20}$alkyl, $C_2$–$C_{20}$alkyl interrupted by oxygen, sulfur or >N—$R_9$; $C_7$–$C_{12}$arylalkyl which is unsubstituted or substituted on the aryl radical by from 1 to 3 $C_1$–$C_4$alkyl groups, $R_7$ and $R_8$ are, independently of one another, hydrogen, $C_1$–$C_{24}$alkyl or $C_2$–$C_{24}$alkyl interrupted by oxygen, sulfur or >N—$R_9$, $R_9$ is hydrogen or $C_1$–$C_8$alkyl, and n is an integer in the range from 1 to 10 for use, as corrosion inhibitors in coating compositions for protecting metal surfaces.

21 Claims, No Drawings

ALKALINE EARTH METAL SALTS, TRANSITION METAL SALTS AND TRANSITION METAL COMPLEXES OF KETOCARBOXYLIC ACIDS AS CORROSION INHIBITORS

The present invention relates to novel alkaline earth metal salts, transition metal salts and transition metal complexes of ketocarboxylic acids, coating compositions comprising an organic film-forming binder, preferably a liquid coating, and the novel corrosion inhibitors, and also the use thereof in coating compositions for protecting metal surfaces.

The use of alkali metal, ammonium and amine salts of ketocarboxylic acids as corrosion inhibitors in aqueous systems is known and described, for example, in U.S. Pat. No. 4,909,987, EP-A-4 12 933 or EP-A-496 555.

It has now been found that alkaline earth metal salts, transition metal salts and transition metal complexes of ketocarboxylic acids are particularly suitable for use as corrosion inhibitors in coating compositions for protecting metal surfaces.

The present invention accordingly provides alkaline earth metal salts, transition metal salts and transition metal complexes of compounds of the formula I

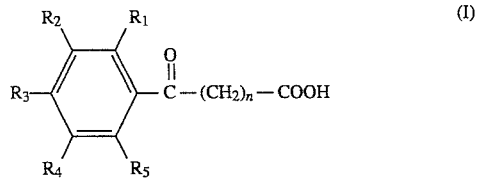

in which $R_1$, $R_2$, $R_3$, $R_4$ and $R_5$ are, independently of one another, hydrogen, halogen, nitro, cyano, $CF_3$, $C_1$–$C_{15}$alkyl, $C_5$–$C_{12}$cycloalkyl, $C_2$–$C_{15}$alkenyl, $C_1$–$C_{12}$haloalkyl, $C_1$–$C_{12}$alkoxy, $C_1$–$C_{12}$alkylthio, $C_6$–$C_{10}$aryl which is unsubstituted or substituted by $C_1$–$C_4$alkyl; $C_6$–$C_{10}$aryloxy which is unsubstituted or substituted by $C_1$–$C_4$alkyl; $C_7$–$C_{12}$arylalkyl which is unsubstituted or substituted on the aryl radical by from 1 to 3 $C_1$–$C_4$alkyl groups; —$CO_2R_6$, —$COR_6$ or

where at least one of the radicals $R_1$ to $R_5$ is hydrogen, halogen or $C_1$–$C_{15}$alkyl, in addition the radicals $R_1$ and $R_2$, $R_2$ and $R_3$, $R_3$ and $R_4$ or $R_4$ and $R_5$ form, together with the carbon atoms to which they are bound, a benzo or cyclohexenyl ring, $R_6$ is $C_1$–$C_{20}$alkyl, $C_2$–$C_{20}$alkyl interrupted by oxygen, sulfur or >N—$R_9$; $C_7$–$C_{12}$arylalkyl which is unsubstituted or substituted on the aryl radical by from 1 to 3 $C_1$–$C_4$alkyl groups, $R_7$ and $R_8$ are, independently of one another, hydrogen, $C_1$–$C_{24}$alkyl or $C_2$–$C_{24}$alkyl interrupted by oxygen, sulfur or >N—$R_9$, $R_9$ is hydrogen or $C_1$–$C_8$alkyl, and n is an integer in the range from 1 to 10.

Halogen is, for example, fluorine, chlorine, bromine or iodine. Preference is given to fluorine, chlorine or bromine, in particular chlorine or bromine.

Alkyl having up to 24 carbon atoms is a branched or unbranched radical, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl or docosyl.

$C_5$–$C_{12}$Cycloalkyl is, for example, cyclopentyl, cyclohexyl, cycloheptyl, cyclooctyl, cyclodecyl or cyclododecyl. Preference is given to cyclohexyl.

Alkenyl having from 2 to 15 carbon atoms is a branched or unbranched radical, for example vinyl, 2-propenyl (allyl), 2-butenyl, 3-butenyl, isobutenyl, n-2,4-pentadienyl, 3-methyl-2-butenyl, n-2-octenyl, n-2-dodecenyl or iso-dodecenyl.

Haloalkyl having up to 12 carbon atoms is a branched or unbranched radical, for example chloromethyl, bromoethyl, fluoropropyl, chloropentyl, chlorohexyl, chlorooctyl, chlorodecyl or chlorododecyl.

Alkoxy having up to 12 carbon atoms is a branched or unbranched radical, for example methoxy, ethoxy, propoxy, isopropoxy, n-butoxy, isobutoxy, pentoxy, isopentoxy, hexoxy, heptoxy, octoxy or decyloxy.

Alkylthio having up to 12 carbon atoms is a branched or unbranched radical, for example methylthio, ethylthio, propylthio, isopropylthio, n-butylthio, isobutylthio, pentylthio, isopentylthio, hexylthio, heptylthio, octylthio, decylthio or dodecylthio.

$C_6$–$C_{10}$Aryl which is unsubstituted or substituted by $C_1$–$C_4$alkyl and bears preferably from 1 to 3, in particular 1 or 2, alkyl groups is, for example, phenyl, naphthyl, o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tertbutylphenyl, 2-ethylphenyl, 2,6-diethylphenyl, 2-methylnaphthyl, 1-methylnaphthyl, 4-methylnaphthyl, 2-ethylnaphthyl or 2,6-diethylnaphthyl.

$C_6$–$C_{10}$Aryloxy which is unsubstituted or substituted by $C_1$–$C_4$alkyl and bears preferably from 1 to 3, in particular 1 or 2, alkyl groups is, for example, phenoxy, naphthoxy, o-, m- or p-methylphenoxy, 2,3-dimethylphenoxy, 2,4-dimethylphenoxy, 2,5-dimethylphenoxy, 2,6-dimethylphenoxy, 3,4-dimethylphenoxy, 3,5-dimethylphenoxy, 2-methyl-6-ethylphenoxy, 4-tert-butylphenoxy, 2-ethylphenoxy, 2,6-diethylphenoxy, 2-methylnaphthoxy, 1-methylnaphthoxy, 4-methylnaphthoxy, 2-ethylnaphthoxy or 2,6-diethylnaphthoxy.

$C_7$–$C_{12}$Arylalkyl which is unsubstituted or substituted on the aryl radical by from 1 to 3 $C_1$–$C_4$alkyl groups is, for example, phenyl-$C_1$–$C_6$alkyl or naphthyl-$C_1$–$C_2$alkyl such as benzyl, 4-methylbenzyl, 4-tert-butylbenzyl, 2,4-dimethylbenzyl, α-methylbenzyl, α,α-dimethylbenzyl, 2-phenylethyl, 2-naphthylmethyl, 1-naphthylmethyl, 1-naphthylethyl or 2-naphthylethyl. Preference is given to benzyl.

Alkyl having from 2 to 24 carbon atoms and interrupted by oxygen, sulfur or >N—$R_9$ is, for example, $CH_3$—O—$CH_2$—, $CH_3$—S—$CH_2$—, $CH_3$—NH—$CH_2$—, $CH_3$—N(CH$_3$)—$CH_2$—, $CH_3$—O—$CH_2CH_2$—O—$CH_2$—, $CH_3$—(O—$CH_2CH_2$—)$_2$O—$CH_2$—, $CH_3$—(O—$CH_2CH_2$—)$_3$O—$CH_2$—or $CH_3$—(O—$CH_2CH_2$—)$_4$O—$CH_2$—.

The alkaline earth metals are, for example, magnesium, calcium, strontium or barium. Preference is given to calcium.

The transition metals are the elements 21 to 30, 39 to 48 and 57 to 80 of the Periodic Table. Preference is given to titanium, manganese, iron, cobalt, zinc, yttrium, zirconium, lanthanum or cerium. Specific preference is given to zirconium.

Preference is given to compounds of the formula I in which $R_1$, $R_2$, $R_3$, $R_4$ and $R_5$ are, independently of one another, hydrogen, halogen, nitro, cyano, $CF_3$, $C_1$–$C_{15}$alkyl, $C_5$–$C_{12}$cycloalkyl, $C_2$–$C_{15}$alkenyl, $C_1$–$C_{12}$haloalkyl, $C_1$–$C_{12}$alkoxy, $C_1$–$C_{12}$alkylthio, $C_6$–$C_{10}$aryl, $C_6$–$C_{10}$aryloxy, $C_7$–$C_{12}$arylalkyl, —$CO_2R_6$, —$COR_6$ or

where at least one of the radicals $R_1$ to $R_5$ is hydrogen, halogen or $C_1$–$C_{15}$alkyl, in addition the radicals $R_1$ and $R_2$, $R_2$ and $R_3$, $R_3$ and $R_4$ or $R_4$ and $R_5$ form, together with the carbon atoms to which they are bound, a benzo or cyclohexenyl ring, and $R_6$ is $C_1$–$C_{20}$alkyl, $C_2$–$C_{20}$alkyl interrupted by oxygen, sulfur or >N—$R_9$; or $C_7$–$C_{12}$arylalkyl.

Preference is likewise given to compounds of the formula I in which at least two, in particular 3, of the radicals $R_1$ to $R_5$ are hydrogen.

Preference is also given to compounds of the formula I in which the metals are calcium, titanium, manganese, iron, cobalt, zinc, yttrium, zirconium, lanthanum or cerium.

Preference is likewise given to compounds of the formula I in which the metal is zirconium.

n in formula I is preferably from 1 to 5, in particular 2.

Particular preference is given to compounds of the formula I in which $R_1$ is hydrogen, $R_2$, $R_3$, $R_4$ and $R_5$ are, independently of one another, hydrogen, chlorine, bromine, nitro, cyano, $CF_3$, $C_1$–$C_8$alkyl, $C_5$–$C_7$cycloalkyl, $C_2$–$C_8$alkenyl, $C_1$–$C_8$alkoxy, $C_1$–$C_8$alkylthio, phenyl, phenyloxy, benzyl, —$CO_2R_6$, —$COR_6$ o

$R_6$ is $C_1$–$C_{12}$alkyl, $C_2$–$C_{12}$alkyl interrupted by oxygen; or benzyl, $R_7$ and $R_8$ are, independently of one another, hydrogen, $C_1$–$C_8$alkyl or $C_2$–$C_{12}$alkyl interrupted by oxygen, and n is an integer in the range from 1 to 5.

Particular preference is likewise given to compounds of the formula I in which $R_1$, $R_2$ and $R_4$ are hydrogen, $R_3$ and $R_5$ are, independently of one another, hydrogen, chlorine, bromine, $CF_3$, $C_1$–$C_8$-alkyl, cyclohexyl, $C_1$–$C_8$alkoxy, —$CO_2R_6$, —$COR_6$ or

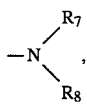

$R_6$ is $C_1$–$C_8$alkyl, $R_7$ and $R_8$ are, independently of one another, hydrogen or $C_1$–$C_8$alkyl, and n is an integer in the range from 2 to 4.

Particular importance is attached to compounds of the formula I in which $R_1$, $R_2$, $R_4$ and $R_5$ are hydrogen and n is 2.

Specific importance is attached to compounds of the formula I in which $R_1$, $R_2$, $R_4$ and $R_5$ are hydrogen, $R_3$ is hydrogen, $C_1$–$C_4$alkyl or chlorine, n is 2 and the metals are calcium, titanium, manganese, iron, cobalt, zinc, yttrium, zirconium, lanthanum or cerium.

Very particular preference is given to the alkaline earth metal salts, transition metal salts and transition metal complexes of 3-(4-methylbenzoyl)propionic acid and 3-(4-chlorobenzoyl)propionic acid.

The alkaline earth metal salts, transition metal salts and transition metal complexes of compounds of the formula I according to the invention can be prepared by methods known per se.

The invention also provides a process for preparing alkaline earth metal salts, transition metal salts and transition metal complexes of compounds of the formula I, which comprises reacting a ketocarboxylic acid of the formula I or an alkali metal salt thereof with an alkaline earth metal or transition metal compound.

In a preferred process, the alkaline earth metal or transition metal compound used is salt, an organometallic compound or an inorganic metal base.

In the preparation of transition metal complexes of the invention, for example zirconium complexes, starting from compounds of the formula I and zirconium carbonate, the reaction is carried out in water without sodium hydroxide solution at elevated temperature, in particular temperatures from 50° to 100° C. Specific preference is given to a temperature range from 70° to 95° C.

However, the reaction can also be carried out in an organic solvent, for example toluene, at slightly elevated temperature. This method is specifically preferred if the alkaline earth metal and transition metal compounds are organometallic compounds. The reaction is preferably carried out in a temperature range from 20° to 70° C., in particular from 40° to 60° C.

The compounds of the formula I (free acids) are preferably used in equimolar amounts with alkaline earth and transition metal compounds. The alkaline earth metal salts, transition metal salts and transition metal complexes of compounds of the formula I according to the invention can have, for example, the general formula II

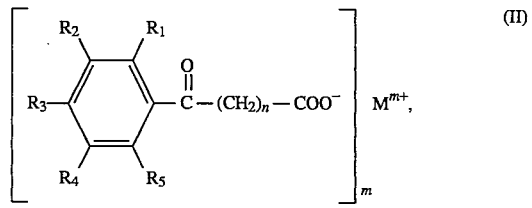

in which M is an alkaline earth or transition metal and m is 2, 3 or 4.

In the case of transition metal salts and transition metal complexes, in particular of the metals zirconium and titanium, particularly when reaction is not equimolar, the end compounds can also have structures deviating from the formula n. Examples thereof are given below for zirconlure complexes.

In the case of transition metal complexes of the invention, in particular of zirconium and titanium complexes, the compounds of the formula I (free acids) can be used in an excess, equimolar or deficient amount in relation to the zirconium or titanium compound used. The molar ratio of ketocarboxylic acid of the formula I to the transition metal compound can be from 20:1 to 1:10. Preference is given to a ratio from 10:1 to 1:3.

Accordingly, the present invention also provides a process for preparing compounds of the invention, wherein the molar ratio of the ketocarboxylic acid of the formula I to the transition metal compound is from 20:1 to 1:10.

In a specifically preferred process for preparing compounds of the invention, the transition metal compound is a zirconium or titanium compound.

The alkaline earth metal salts, transition metal salts and transition metal complexes of compounds of the formula I according to the invention can also be further complexed by free acid (formula I), water or by other anions such as hydroxides which are present in the reaction medium. In the case of metal acetates or metal alkoxides, the acetate or alkoxide anions can be present in the compounds of the formula I according to the invention.

On the basis of the above observations, the percentage metal content by weight of the compounds of the formula I according to the invention can be different. Thus, the particularly preferred zirconium complexes of 3-(4-methylbenzoyl)propionic acid according to the invention can have a zirconium content from 5 to 50 % by weight, preferably from 10 to 40 %.

The structure of the zirconium complexes of the invention has not been completely clarified. The empirical formulae of the zirconium complexes of 3-(4-methylbenzoyl)propionic acid according to the invention (R=3-(4-methylbenzoyl)propionate) are, for example (cf. Examples 2 to 14): $ZrO(OH)(O_2CR) \cdot 6.6$ $HO_2CR$; $ZrO(OH)(O_2CR) \cdot 2.9$ $HO_2CR$; $ZrO(OH)(O_2CR) \cdot 0.3$ $HO_2CR$; $ZrO(OH)(O_2CR) \cdot 0.7$ $HO_2CR$; $ZrO(OH)(O_2CR)_{0.8}(acetate)_{0.2}$; $ZrO(OH)(O_2CR)_{0.5}(acetate)_{0.5}$; $ZrO(OH)(O_2CR) \cdot 0.3$ $HO_2CR$; $ZrO_2 \cdot ZrO(OH)(O_2CR)$; $Zr(OC_3H_7)_3(O_2CR)$; $ZrO(OH)(O_2CR) \cdot 0.48$ $HO_2CR$; $Zr(OC_3H_7)_2(O_2CR)_2$; $Zr(OC_4H_9)_3(O_2CR)$ or $Zr(OC_3H_7)_3(O_2CR)$.

Accordingly, the present invention also provides products obtainable by reacting a compound of the formula I or an alkali metal salt thereof with an alkaline earth metal or transition metal compound.

Particular preference is given to dissolving a compound of the formula I with a base, for example at least one equivalent of an aqueous alkali metal hydroxide solution, and subsequently treating it with an aqueous solution of an alkaline earth metal or transition metal compound. The compounds of the formula I according to the invention are filtered or extracted from the reaction medium with an organic solvent, for example ethyl acetate or dichloromethane.

The compounds of the formula I (free acids and not the salts and complexes of the invention) are known and many are commercially available or can be prepared as described in Houben-Weyl, Methoden der Organischen Chemie, Volume VIII, pp. 381–382 (1952) and Volume E5, pp. 398–399 (1985). Thus, for example, the Friedel-Crafts acylation of substituted aromatics (benzene and naphthalene derivatives) with cyclic anhydrides gives the compounds of the formula I in excellent yields.

The alkaline earth metal or transition metal compounds used are, for example, salts, organometallic compounds or inorganic metal bases or mixtures thereof.

Examples of salts are halides (in particular chlorides), nitrates, carbonates, sulfates, where these may also be basic salts, for example lanthanum chloride, yttrium chloride, iron chloride, titanium tetrachloride, zinc chloride, calcium chloride, manganese chloride, cobalt chloride, cerium chloride, zinc nitrate, manganese nitrate, cobalt nitrate, cerium nitrate, iron nitrate, calcium nitrate, lanthanum nitrate, yttrium nitrate, zirconium sulfate, iron sulfate, manganese sulfate, cobalt sulfate, cerium sulfate, zirconium oxide chloride, titanium oxide chloride, zirconlure acetate, zinc acetate, manganese acetate, cobalt acetate, lanthanum acetate, calcium acetate, zirconium carbonate, zinc carbonate, manganese carbonate, cobalt carboante and calcium carbonate.

Examples of organometallic compounds are in particular alkoxides, for example zirconium n-propoxide, zirconium isopropoxide, zirkonium n-butoxide, titanium n-propoxide, titanium, isopropoxide, titanium ethoxide and titanium n-butoxide.

Examples of inorganic metal bases are hydroxides, oxides and amides, for example calcium hydroxide, calcium oxide and calcium amide.

The alkali metal hydroxide solution used is potassium hydroxide or sodium hydroxide solution, preferably sodium hydroxide solution.

The precipitation of the alkaline earth metal salts and transition metal complexes of the formula I according to the invention is preferably carried out at room temperature.

The alkaline earth metal salts, transition metal salts and transition metal complexes of compounds of the formula I according to the invention are suitable for use as corrosion inhibitors in coating compositions for protecting metal surfaces and also for pretreating metallic substrates. As such they can be added to any liquid or solid organic material.

Accordingly, the invention also provides coating compositions comprising a) an organic film-forming binder and b) at least one alkaline earth metal salt, transition metal salt or transition metal complex of compounds of the formula I.

The coating composition is preferably a liquid. Specific preference is given to a water-based liquid.

Liquid coatings are, for example, lacquers, paints or varnishes. These always comprise an organic film-forming binder as well as other, optional components.

Preferred organic film-forming binders are epoxy resins, polyurethane resins, polyester resins, acrylic resins and copolymer resins thereof, polyvinyl resins, phenolic resins, alkyd resins or mixtures of such resins.

Suitable organic film-forming binders for the coating composition are conventional film formers for solvent-containing, but in particular for water-based, paint compositions. Examples of such film formers are epoxy resins, polyurethane resins, amino resins or mixtures of such resins; a basic aqueous dispersion or a solution of an acid resin.

Particularly important are organic film-forming binders for water-based coating compositions, for example alkyd resins; acrylic resins; 2-component epoxy resins; polyurethane resins; polyester resins which are customarily saturated; water-dilutable phenolic resins or derived dispersions; water-dilutable urea resins; resins based on vinyl/acrylic copolymers.

Viewed more specifically, the alkyd resins can be water-dilutable alkyd resin systems which can be used in air drying form or in the form of stoving systems, if desired in combination with water-dilutable melamine resins; the alkyd resins can also be oxidatively drying, air drying or storing systems which are, if desired, used in combination with aqueous dispersions based on acrylic resins or copolymers thereof, with vinyl acetates etc.

The acrylic resins can be pure acrylic resins, acrylic ester copolymers, combinations with vinyl resins or copolymers with vinyl monomers such as vinyl acetate, styrene or butadiene. These systems can be air drying systems or stoving systems.

Water-dilutable epoxy resins in combination with suitable polyamine crosslinkers have excellent mechanical strength and chemical resistance. When using liquid epoxy resins, no addition of organic solvent to aqueous systems is necessary. The use of solid resins or solid resin dispersions normally requires an addition of small amounts of solvent to improve film formation.

Preferred epoxy resins are those based on aromatic polyols, in particular those based on bisphenols. The epoxy resins are used in combination with crosslinkers. The latter can be, in particular, amino- or hydroxy-functional compounds, an acid, an acid anhydride or a Lewis acid. Examples of these are polyamines, polyaminoamides, polymers based on polysulfides, polyphenols, boron fluorides and complex compounds thereof, polycarboxylic acids, 1,2-dicarboxylic anhydrides or pyromellitic dianhydride.

Polyurethane resins are derived, on the one hand, from polyethers, polyesters and polybutadienes having terminal hydroxyl groups and, on the other hand, from aliphatic or aromatic polyisocyanates.

Suitable polyvinyl resins are, for example, polyvinyl butyral, polyvinyl acetate or copolymers thereof.

Suitable phenolic resins are synthetic resins in the structure of which phenols are the main component, thus in particular phenol-, cresol-, xylenol- and resorcinol-formaldehyde resins, alkylphenolic resins and also condensation products of phenols with acetaldehyde, furfurol, acrolein or other aldehydes. Modified phenolic resins are also of importance.

The coating compositions can additionally comprise one or more components selected from pigments, dyes, fillers, flow modifiers, dispersants, thixotropes, adhesion promoters, antioxidants, light stabilizers or curing catalysts. They can also comprise other known corrosion protection compositions, for example corrosion protection pigments, such as phosphate- or borate-containing pigments or metal oxide pigments, or other organic or inorganic corrosion inhibitors, for example salts of nitroisophthalic acid, phosphoric esters, industrial amines or substituted benzotriazoles.

The pigments are, for example, titanium dioxide, iron oxide, aluminium bronze or phthalocyanine blue.

Examples of fillers are talc, aluminium oxide, aluminium silicate, baryte, mica or silicon dioxide. The corrosion inhibitors of the invention can also be applied to a carrier. Pulverulent fillers or pigments are particularly suitable for this purpose.

Flow modifiers and thixotropes are based on modified bentonites.

Adhesion promoters are based on modified silanes.

Also advantageous is the addition of basic fillers or pigments which in certain binder systems have a synergistic effect on the corrosion inhibition. Examples of such basic fillers and pigments are calcium or magnesium carbonate, zinc oxide, zinc carbonate, zinc phosphate, magnesium oxide, aluminium oxide, aluminium phosphate or mixtures thereof. Examples of basic organic pigments are those based on aminoanthraquinone.

The corrosion inhibitors of the invention can be added to the coating during the preparation thereof, for example during pigment dispersion by milling, or the inhibitor is dissolved in a solvent and subsequently stirred into the coating composition. The corrosion inhibitors of the invention can likewise be used for pretreatment of the metal surface.

The alkaline earth metal salts, transition metal salts and transition metal complexes of compounds of the formula I according to the invention are advantageously used in an amount from 0.01 to 20% by weight, preferably from 0.05 to 5% by weight, based on the total weight of the coating composition.

The coatings can be applied to the substrate by conventional methods, for example by spraying, dipping, painting on or by electrodeposition. Often a plurality of coats is applied. The corrosion inhibitors are first and foremost added to the primer, since they act in particular at the metal/paint interface. However, they can also be additionally added to the intermediate or topcoat. Depending on whether the binder is a physically, chemically or oxidatively drying resin or a heat or radiation curing resin, the curing of the coating is carried out at room temperature or by heating (storing) or by irradiation.

Preferably the coating is a primer for metallic substrates, for example iron, steel, copper, zinc or aluminium, and also alloys thereof.

In addition to the anticorrosive action, the alkaline earth metal salts and transition metal complexes of compounds of the formula I according to the invention have the advantage that they favourably affect the paint/metal adhesion and have no negative effects on the shelf-life of the coating compositions of the invention.

Accordingly, a preferred embodiment of the present invention is the use of the alkaline earth metal salts, transition metal salts and transition metal complexes of compounds of the formula I as corrosion inhibitors in coating compositions for metal surfaces.

The present invention also provides a process for protecting a corrodable metal substrate, which comprises applying to said substrate a coating composition comprising a) an organic film-forming binder and b) as corrosion inhibitor at least one alkaline earth metal salt, a transition metal salt or a transition metal complex of compounds of the formula I and subsequently drying and/or curing the coating.

The following examples illustrate the invention. Parts and percentages are by weight.

EXAMPLE 1

Preparation of the zinc salt of 3-(4-methylbenzoyl)propionic acid (compound (101), Table 1).

A solution of 59.5 g (0.20 mol) of zinc nitrate hexahydrate $[Zn(NO_3)_2 6H_2O]$ in 200 ml of water is added dropwise to a solution of 38.4 g (0.20 mol) of 3-(4-methylbenzoyl)propionic acid in 200 ml of 1.0N sodium hydroxide solution while stirring well. The precipitate is filtered off, washed well with water a number of times and dried in a vacuum oven at 50° C. The zinc salt of 3-(4-methylbenzoyl)propionic acid, mp. ~220° C. (compound (101), Table 1 ) is obtained.

The procedure described in Example I is repeated, using manganese nitrate, cobalt nitrate, cerium nitrate, iron nitrate, lanthanum chloride, yttrium chloride and calcium nitrate with 3-(4-methylbenzoyl)propionic acid to prepare the compounds (102) to (108) (cf. Table 1).

TABLE 1

| No. | Metal salt | compound of the invention | M.p. (°C.) | C(%), (calculated/found) | H (%) | % $H_2O$ |
|---|---|---|---|---|---|---|
| 101 | $Zn(NO_3)_2$ | $Zn(OOCR)_2$ | ~220 | 59.01 58.94 | 4.95 4.85 | 0.3 |
| 102 | $Mn(NO_3)_2$ | $Mn(OOCR)_2$ | >250 | 60.42 59.87 | 5.07 5.18 | 2.1 |
| 103 | $Co(NO_3)_2$ | $Co(OOCR)_2$ | ~80 | 59.87 | 5.02 | |

TABLE 1-continued

| No. | Metal salt | compound of the invention | M.p. (°C.) | C(%), H (%) (calculated/found) | | % H₂O |
|---|---|---|---|---|---|---|
| | | | | 58.43 | 5.20 | |
| 104 | Ce(NO₃)₃ | Ce(OOCR)₃ | 161 | 55.48 | 4.62 | 2.6 |
| | | | | 54.20 | 4.73 | |
| 105 | Fe(NO₃)₃ | Fe(OOCR)₃ | 94 | 63.02 | 5.29 | 2.2 |
| | | | | 60.80 | 5.44 | |
| 106 | LaCl₃ | La(OOCR)₃ | 165 | 55.62 | 4.63 | 2.7 |
| | | | | 54.61 | 4.82 | |
| 107 | YCl₃ | Y(OOCR)₃ | 148 | 59.83 | 5.01 | 4.5 |
| | | | | 57.07 | 5.24 | |
| 108 | Ca(NO₃)₂ | Ca(OOCR)₂·2H₂O | 122 | 57.64 | 5.67 | 7.8 |
| | | | | 58.40 | 5.61 | |

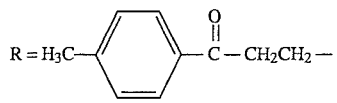

The definition of R in Table 1 also applies to Examples 2 to 14 and 16.

EXAMPLE 2

Preparation of the zirconium complex of 3-(4-methylbenzoyl)propionic acid (compound (109)) using zirconium sulfate.

A solution of 18.3 g (0.05 mol) of zirconium surfate (22.8% zirconium) in 40 ml of water is added dropwise to a solution of 19.2 g (0.10 mol) of 3-(4-methylbenzoyl)propionic acid in 100 ml of 1.0 N sodium hydroxide solution while stirring well. The precipitate is filtered off, washed well with water a number of times and dried in a vacuum oven at 50° C. The zirconium complex of 3-(4-methylbenzoyl)propionic acid (compound (109)) is obtained. Elemental analysis calculated for ZrO(OH)(O₂CR)·6.6 HO₂CR: Zr 5.8%; C 63.4%; H 5.8%; HO₂CR 80.1%. Found: Zr 7.4%; C 58.6%; H 5.6%; H₂O 2.3%; HO₂CR 79.8%.

EXAMPLE 3

Preparation of the zirconium complex of 3-(4-methylbenzoyl)propionic acid (compound (110)) using zirconium sulfate.

A solution of 35.5 g (0.089 mol) of zirconium sulfate (22.8% zirconium) in 70 ml of water is added dropwise to a solution of 76.9 g (0.40 tool) of 3-(4-methylbenzoyl)propionic acid in 400 ml of 1.0N sodium hydroxide solution while stirring well. The precipitate is filtered off, washed well with water a number of times and dried in a vacuum oven at 50° C. The zirconium complex of 3-(4-methylbenzoyl)propionic acid (compound (110)) is obtained. Elemental analysis calculated for ZrO(OH)(O₂CR)·2.9 HO₂CR: Zr 10.4%; C 59.0%; H 5.4%; HO₂CR 63.8%. Found: Zr 9.4%; C 58.3%; H 5.4%; H₂O 2.0%; HO₂CR 64.2%.

EXAMPLE 4

Preparation of the zirconium complex of 3-(4-methylbenzoyl)propionic acid (compound (111)) using zirconium oxide chloride.

A solution of 28.1 g (0.115 mol) of zirconium oxide chloride (37.2% zirconium) in 55 ml of water is added dropwise to a solution of 57.7 g (0.30 tool) of 3-(4-methylbenzoyl)propionic acid in 300 ml of 1.0N sodium hydroxide solution while stirring well. The precipitate is filtered off, washed well with water a number of times and dried in a vacuum oven at 50° C. The zirconium complex of 3-(4-methylbenzoyl)propionic acid (compound (111)) is obtained. Elemental analysis calculated for ZrO(OH)(O₂CR)·0.3 HO₂CR: Zr 24.5%; C 46.0%; H 4.2%; HO₂CR 15.5%. Found: Zr 25.2%; C 48.8%; H 4.6%; H₂O 3.2%; HO₂CR 8.7%.

EXAMPLE 5

Preparation of the zirconium complex of 3-(4-methylbenzoyl)propionic acid (compound (112)) using zirconium oxide chloride.

A solution of 14.3 g (0.058 mol) of zirconium oxide chloride (37.2% zirconium) in 30 ml of water is added dropwise to a solution of 19.2 g (0.10 mol) of 3-(4-methylbenzoyl)propionic acid in 100 ml of 1.0N sodium hydroxide solution while stirring well. The precipitate is filtered off, washed well with water a number of times and dried in a vacuum oven at 50° C. The zirconium complex of 3-(4-methylbenzoyl)propionic acid (compound (112)) is obtained. Elemental analysis calculated for ZrO(OH)(O₂CR)·0.7 HO₂CR: Zr 20.3%; C 49.9%; H 4.6%; HO₂CR 29.9%. Found: Zr 19.2%; C 48.3%; H 4.7%; H₂O 5.5%; HO₂CR 40.0%.

EXAMPLE 6

Preparation of the zirconium complex of 3-(4-methylbenzoyl)propionic acid (compound (113)) using zirconium acetate.

A solution of 37.2 g (0.075 mol) of zirconium acetate (18.4% zirconium) in 60 ml of water is added dropwise to a solution of 19.2 g (0.10 mol) of 3-(4-methylbenzoyl)propionic acid in 100 ml of 1.0N sodium hydroxide solution while stirring well. The precipitate is filtered off, washed well with water a number of times and dried in a vacuum oven at 50° C. The zirconium complex of 3-(4-methylbenzoyl)propionic acid (compound (113)) is obtained. Elemental analysis calculated for ZrO(OH)(O₂CR)₀.₈(acetate)₀.₂: Zr 31.6%; C 38.2%; H 3.6%; acetate 4.1%. Found: Zr 32.6%; C 38.6%; H 4.1%; H₂O 2.5%; acetate 5.7%.

EXAMPLE 7

Preparation of the zirconium complex of 3-(4-methylbenzoyl)propionic acid (compound (114)) using zirconium acetate.

A solution of 148.8 g (0.30 mol) of zirconium acetate (18.4% zirconium) in 100 ml of water is added dropwise to a solution of 9.60 g (0.05 tool) of 3-(4-methylbenzoyl)propionic acid in 50 ml of 1.0N sodium hydroxide solution while stirring well. The precipitate is filtered off, washed well with water a number of times and dried in a vacuum oven at 50° C. The zirconium complex of 3-(4-methylbenzoyl)propionic acid (compound (114)) is obtained. Elemental analysis calculated for $ZrO(OH)(O_2CR)_{0.5}(acetate)_{0.5}$: Zr 36.6%; C 31.3%; H 3.2%; acetate 11.8%. Found: Zr 34.9%; C 29.7%; H 3.8%; $H_2O$ 3.2%; acetate 12.8%.

EXAMPLE 8

Preparation of the zirconium complex of 3-(4-methylbenzoyl)propionic acid (compound (115)) using zirconium carbonate.

A suspension of 15.0 g (56.0 mmol) of zirconium carbonate (34 % zirconium) and 15.0 g (78.0 mmol) of 3-(4-methylbenzoyl)propionic acid in 150 ml of water is heated at 90° C. for 2 hours with intensive stirring. Subsequently the reaction mixture is cooled, the water is decanted off and the residue is extracted with ethyl acetate. The solvent is evaporated on a rotary evaporator and the residue is dried in high vacuum at 50° C. The zirconium complex of 3-(4-methylbenzoyl)propionic acid (compound (115)) is obtained. Elemental analysis calculated for $ZrO(OH)(O_2CR)\cdot 0.3\ HO_2CR$: Zr 24.5%; C 46.0%; H 4.2%; $HO_2CR$ 15.5%. Found: Zr 21.0%; C 48.1%; H 4.6%; $H_2O$ 0.4%; $HO_2CR$ 16.5%.

EXAMPLE 9

Preparation of the zirconium complex of 3-(4-methylbenzoyl)propionic acid (compound (116)) using zirconium carbonate.

A suspension of 45.0 g (168 mmol) of zirconium carbonate (34% zirconium) and 15.0 g (78.0 mmol) of 3-(4-methylbenzoyl)propionic acid in 150 ml of water is heated at 90° C. for 2 hours with intensive stirring. Subsequently the reaction mixture is cooled, the water is decanted off, the residue is extracted with ethyl acetate and the residue is dried in high vacuum at 50° C. The zirconium complex of 3-(4-methylbenzoyl)propionic acid (compound (116)) is obtained. Elemental analysis calculated for $ZrO_2 \cdot ZrO(OH)(O_2CR)$: Zr 41.6%; C 30.1%; H 4.6%. Found: Zr 37.7%; C 26.8%; H3.7%; $H_2O$ 2.7%.

EXAMPLE 10

Preparation of the zirconium complex of 3-(4-methylbenzoyl)propionic acid (compound (117)) using zirconium n-propoxide.

A solution of 44.3 g (0.10 mol) of zirconium n-propoxide (20.6% zirconium) and 19.2 g (0.10 mol) of 3-(4-methylbenzoyl)propionic acid in 200 ml of dry toluene is stirred at 50° C. for 12 hours under a nitrogen atmosphere. Subsequently the reaction mixture is cooled and evaporated on a rotary evaporator and the residue is dried in high vacuum at 50° C. The zirconium complex of 3-(4-methylbenzoyl)propionic acid (compound (117)) is obtained. Elemental analysis calculated for $Zr(OC_3H_7)_3(O_2CR)$: Zr 19.8%; C 52.2%; H 7.03%. Found: Zr 20.0%; C 52.4%; H 6.75%.

EXAMPLE 11

Preparation of the zirconium complex of 3-(4-methylbenzoyl)propionic acid (compound (118)) using zirconium carbonate.

A suspension of 50 g (0.18 mol) of zirconium carbonate (32.8% zirconium) and 50 g (0.26 mol) of 3-(4-methylbenzoyl)propionic acid in 500 ml of water and 500 ml of toluene is heated at 83° C. for 30 minutes with intensive stirring. The reaction mixture is subsequently stirred for a further 45 minutes at 83° C. The organic phase is separated off while still warm and evaporated on a rotary evaporator to a residual volume of 200 mi. 2,000 ml of petroleum spirit are subsequently added to the solution with intensive stirring. The precipitate formed is filtered off and dried in high vacuum at 50° C. The zirconium complex of 3-(4-methylbenzoyl)propionic acid (compound (118)) is obtained. Elemental analysis calculated for $ZrO(OH)(O_2CR)\cdot 0.48\ HO_2CR$: Zr 22.4%; C 47.9%; H 4.4%; $HO_2CR$ 22.6%. Found: Zr 22.2%; C 47.7%; H 4.8%; $H_2O$ 0.75%; $HO_2CR$ 20.0%.

EXAMPLE 12

Preparation of the zirconium complex of 3-(4-methylbenzoyl)propionic acid (compound (119)) using zirconium n-propoxide.

A solution of 44.3 g (0.10 mol) of zirconium n-propoxide (20.6 % zirconium) and 38.4 g (0.20 mol) of 3-(4-methylbenzoyl)propionic acid in 200 ml of dry toluene is stirred at 50° C. for 12 hours under a nitrogen atmosphere. Subsequently the reaction mixture is cooled and evaporated on a rotary evaporator and the residue is dried in high vacuum at 50° C. The zirconium complex of 3-(4-methylbenzoyl)propionic acid (compound (119)) is obtained. Elemental analysis calculated for $Zr(OC_3H_7)2(O_2CR)_2$: Zr 15.4%; C 56.8%; H 6.1%. Found: Zr 15.1%; C 56.7%; H 6.2%.

EXAMPLE 13

Preparation of the zirconium complex of 3-(4-methylbenzoyl)propionic acid (compound (120)) using zirconium n-butoxide.

A solution of 43.2 g (0.10 mol) of zirconium n-butoxide (21.1% zirconium) and 19.2 g (0.10 mol) of 3-(4-methylbenzoyl)propionic acid in 200 ml of dry toluene is stirred at 50° C. for 12 hours under a nitrogen atmosphere. Subsequently the reaction mixture is cooled and evaporated on a rotary evaporator and the residue is dried in high vacuum at 50° C. The zirconium complex of 3-(4-methylbenzoyl)propionic acid (compound (120)) is obtained. Elemental analysis calculated for $Zr(OC_4H_9)_3(O_2CR)$: Zr 18.2%; C 55.0%; H 7.6%. Found: Zr 19.3%; C 54.2%; H 7.0%.

EXAMPLE 14

Preparation of the zirconium complex of 3-(4-methylbenzoyl)propionic acid (compound (121)) using zirconium i-propoxide.

A solution of 17.3 g (0.05 mol) of zirconium i-propoxide (26.4% zirconium) and 9.6 g (0.05 mol) of 3-(4-methylbenzoyl)propionic acid in 200 ml of dry toluene is stirred at 50° C. for 12 hours under a nitrogen atmosphere. Subsequently the reaction mixture is cooled and evaporated on a rotary evaporator and the residue is dried in high vacuum at 50° C. The zirconium complex of 3-(4-methylbenzoyl)propionic acid (compound (121)) is obtained. Elemental analysis calculated for $Zr(OC_3H_7)_3(O_2CR)$: Zr 19.8%; C 52.2%; H 7.0%. Found: Zr 23.8%; C 47.4%; H 5.8%.

EXAMPLE 15

Preparation of the zirconium complex of 3-(4-chlorobenzoyl)propionic acid (compound (122)) using zirconium carbonate.

A suspension of 30 g (0.108 mol) of zirconium carbonate (32.8% zirconium) and 33.2 g (0.156 mol) of 3-(4-chlorobenzoyl)propionic acid in 300 ml of water is heated at 90° C. for 30 minutes with intensive stirring. The reaction mixture is subsequently stirred for a further 45 minutes at 90° C. The water is then decanted off hot and the residue is extracted with ethyl acetate. The solvent is evaporated on a rotary evaporator and the residue is dried in high vacuum at 50° C. The zirconium complex of 3-(4-chlorobenzoyl)propionic acid (compound (122)) is obtained. Elemental analysis calculated for ZrO(OH)(O$_2$CR')·0.47 HO$_2$CR': Zr 20.9%; C 40.5%; H 3.1%; Cl 12.0%; HO$_2$CR' 22.9%. Found: Zr 20.7%; C 40.1%; H 3.3%; Cl 11.6%; H20 0.6 %; HO$_2$CR' 29.7%.

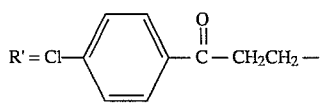

EXAMPLE 16

Preparation of the titanium complex of 3-(4-methylbenzoyl)propionic acid (compound (123)) using titanium(IV) n-propoxide.

A solution of 14.2 g (50 mmol) of titanium(IV) n-propoxide and 9.61 g (50 mmol) of 3-(4-methylbenzoyl)propionic acid in 100 ml of dry toluene is stirred at 50° C. for 12 hours under a nitrogen atmosphere. Subsequently the reaction mixture is cooled and evaporated on a rotary evaporator and the residue is dried in high vacuum at 50° C. The titanium complex of 3-(4-methylbenzoyl)propionic acid (compound (123)) is obtained. Elemental analysis calculated for Ti(OC$_3$H$_7$)$_3$(O$_2$CR): Ti 11.5%; C 57.7%; H 7.8%. Found: Ti 11.5%; C 56.5%; H 7.6%.

EXAMPLE 17

Testing of alkaline earth metal salts, transition metal salts and transition metal complexes of 3-(4-methylbenzoyl)propionic acid as corrosion inhibitors in acrylic dispersions based on Maincote HG-54.

To prepare the coating composition based on Maincote HG-54, the components 1 to 8 (formulation without additives) or the components 1 to 9 (formulation with additive) are added in the indicated order (cf. Table 2).

TABLE 2

| Acrylic dispersion based on Maincote HG-54 | |
|---|---|
| Composition | % by weight |
| 1) Deionized water | 3.10 |
| 2) Methylcarbitol[a] | 5.00 |
| 3) Orotan 165[b] | 0.82 |
| 4) Triton CF 10[c] | 0.29 |
| 5) Drew Plus TS 4380[d] | 0.28 |
| 6) Acrysol RM 8[e] | 0.60 |
| 7) Bayferrox 130 M[f] | 5.72 |
| 8) Millicarb[g] | 17.40 |
| 9) corrosion inhibitor of the invention | |
| 10) Butyl diglycol | 3.67 |
| 11) Maincote HG-54[h] | 58.70 |
| 12) Texanol[i] | 1.50 |
| 13) Dibutyl phthalate[k] | 1.50 |
| 14) Sodium nitrite[l] | 0.80 |
| 15) Drew T 4310[m] | 0.32 |
| 16) Ammonia solution (25%) | 0.30 |
| Total | 100.00 |

Total solids: 47%; pH: 8 to 8.5; a) ®Methylcarbitol: diethylene glycol monomethyl ether (Union Carbide); b) ®Orotan 165: dispersant (Rohm & Haas); c) ®Triton CF 10: nonionic wetting agent (Rohm & Haas); d) ®Drew Plus TS 4380: antifoam (Drew Chem. Corp.); e) ®Acrysol RM 8: nonionic thickener (Rohm& Haas); f) ®Bayferrox 130 M: iron oxide red (Bayer AG); g) ®Millicarb: calcium carbonate (Omya); h) ®Maincote HG-54: acrylic dispersion, 41.5% in aleionized water (Rohm& Haas); i) ®Texanol: coalescent (Eastman Chem. Prod., Inc.); k) Dibutyl phthalate: plasticizer (Eastman Chem. Prod., Inc.); l) sodium nitrite: rust film inhibitor (Fluka); m) ®Drew T 4310: nonionic antifoam (Drew Chem. Corp.).

Using a high-speed stirrer at 3,000 rpm, the components are dispersed to a milled fineness or milled particle size of <15 μm. The dispersion result of the pigment paste thus obtained is assessed by determination of the grindometer value (ISO 1524). The mount used of the corrosion inhibitors of the invention is based on the total solids of the formulation without additive (total solids: 47% ). Accordingly, for example, addition of 1% of corrosion inhibitor in 100 g of dispersion is an amount of 0.47 g. To finish the coating composition, the components 10 to 16 according to Table 2 are added at reduced stirring speed (1,000 rpm) in the indicated order. The pH of the formulation is subsequently monitored and is adjusted, if necessary, with ammonia solution (25 % ) to a value of pH from 8 to 8.5 prior to application.

The coating composition can be applied undiluted by airless spraying or after dilution by painting on, rolling or conventional spraying. For application by conventional spraying, the formulations are diluted to a spraying viscosity from 22 to 23 seconds (Ford cup 4; DIN 53 211). Diluent: butyl glycol/deionized water=1:1 (g/g).

The formulation is applied to steel sheets (10 times 15 cm) of the type Q-Panel R (cold-rolled, untreated steel from: The Q-Panel Company, Cleveland, USA) in a thickness which is 50 μm after drying (drying conditions: 10 days at room temperature).

Prior to the commencement of weathering, defined damage (70 times 0.5 mm) is applied to the coating films in the form of a parallel cut (i.e. parallel to the longest edge of the sheet) using a Bonder scoring apparatus (model 205 from Lau, 5870 Hemer/Germany). The edges of the sheets are protected by application of an edge protector (®Icosit 255 from Inertol AG, Winterthur, Switzerland).

The samples are then subjected to accelerated weathering in the salt spray test (DIN 50 021 SS) for 168 hours and in the condensation test (ASTM D 4585-87) for 330 hours. The results are summarized in Tables 3 to 6. The results are evaluated on the basis of the applicable DIN standards according to an evaluation key by giving a corrosion protection factor (CPF). The CPF is obtained by adding an assessment of the coating (film) and an assessment of the steel, the maximum being 12 points. The individual maximum values for the coating (film) and the steel are 6 points. The larger the numbers, the better the corrosion protection.

TABLE 3

| | Salt spray test, 168 hours | | |
|---|---|---|---|
| Compound | CPF film | CPF metal | CPF |
| — | 2.8 | 3.0 | 5.8 |
| 1% (102) | 3.6 | 3.6 | 7.2 |
| 2% (102) | 4.0 | 4.5 | 8.5 |

TABLE 3-continued

| | Salt spray test, 168 hours | | |
|---|---|---|---|
| Compound | CPF film | CPF metal | CPF |
| 1% (104) | 4.0 | 4.5 | 8.5 |
| 2% (104) | 4.0 | 5.5 | 9.5 |
| 1% (105) | 3.2 | 4.5 | 7.7 |
| 2% (105) | 4.0 | 4.5 | 8.5 |
| 1% (111) | 4.0 | 5.0 | 9.0 |
| 2% (111) | 4.0 | 5.0 | 9.0 |
| 1% (112) | 3.2 | 4.8 | 8.0 |
| 2% (112) | 4.0 | 4.8 | 8.8 |
| 1% (113) | 4.0 | 5.5 | 9.5 |
| 2% (113) | 4.0 | 5.3 | 9.3 |
| 1% (114) | 3.4 | 4.8 | 8.2 |
| 2% (114) | 3.8 | 5.5 | 9.3 |
| 1% (116) | 3.4 | 4.0 | 7.4 |
| 2% (116) | 3.4 | 5.0 | 8.4 |

TABLE 4

| | Salt spray test, 168 hours | | |
|---|---|---|---|
| Compound | CPF film | CPF metal | CPF |
| — | 2.4 | 2.3 | 4.7 |
| 1% (122) | 3.0 | 4.7 | 7.7 |
| 2% (122) | 3.2 | 5.4 | 8.6 |

TABLE 5

| | Condensation test, 330 hours | | |
|---|---|---|---|
| Compound | CPF film | CPF metal | CPF |
| — | 3.2 | 2.0 | 5.2 |
| 1% (107) | 3.4 | 5.5 | 8.9 |

TABLE 6

| | Condensation test, 330 hours | | |
|---|---|---|---|
| Compound | CPF film | CPF metal | CPF |
| — | 2.8 | 2.0 | 4.8 |
| 1% (122) | 3.2 | 5.8 | 9.0 |

EXAMPLE 18

Testing of alkaline earth metal salts, transition metal salts and transition metal complexes of 3-(4-methylbenzoyl)propionic acid as corrosion inhibitors in alkyd resin systems based on Bayhydrol B 130 H.

The procedure described in Example 17 is repeated, preparing the coating composition based on Bayhydrol B 130 H by adding the components 1 to 6 (formulation without additives) or the components 1 to 7 (formulation with additive) in the indicated order (cf. Table 7).

TABLE 7

| Alkyd resin formulation based on Bayhydrol B 130 H | |
|---|---|
| Composition | % by weight |
| 1) Bayhydrol B 130 H[a] | 60.03 |
| 2) Servosyn WEB (8%)[b] | 0.14 |
| 3) Ascinin R[c] | 0.28 |
| 4) Bayferrox 130 M[d] | 21.13 |
| 5) Heladol 10[e] | 5.15 |
| 6) Mikrotalk AT Extra[f] | 10.57 |
| 7) corrosion inhibitor of the invention | |
| 8) Aerosil 300[g] | 0.20 |
| 9) Zinc oxide | 1.06 |
| 10) Butyl glykol | 0.90 |
| 11) Aluminium octoate | 0.05 |
| 12) Deionized water | 0.49 |
| Total | 100.00 |

Total solids: 56.1%; a) ®Bayhydrol B 130 H: 30% in aleionized water, alkyd resin, water-dilutable (Bayer AG); b) ®Servosyn WEM (8%): cobalt dryer (8% metal) (Servo Delden B.V.); c) ®Ascinin R: skin inhibitor based on oxime (Bayer AG); d) ®Bayferrox 130M: iron oxide red (Bayer AG); e) ®Heladol 10: calcium carbonate (Lange); f) Mikrotalk AT Extra: micronized talc (Norwegian); g) ®Aerosil 300: thickener and thixotrope, chemically pure silica (Degussa).

The components are dispersed to a fineness or particle size of <15 μm either by using a high-speed stirrer at 3,000 rpm or by using, for example, a horizontal ball mill. The dispersion result of the pigment paste thus obtained is assessed by determination of the grindometer value (ISO 1524). The amount used of the corrosion inhibitors of the invention is based on the total solids of the formulation without additive (total solids: 56.1%). Accordingly, for example, addition of 1% of corrosion inhibitor in 100 g of formulation is an amount of 0.56 g. To finish the coating composition, the components 8 to 12 according to Table 7 are added at reduced stirring speed (1,000 rpm) in the indicated order.

The application of the formulation to steel sheets of the type Q-Panel R, the salt spray test (168 hours) and the determination of the corrosion protection factors CPF are carried out as described in Example 17. The results am summarized in Table 8. The larger the numbers, the better the corrosion protection.

TABLE 8

| | Salt spray test, 168 hours | | |
|---|---|---|---|
| Compound | CPF film | CPF metal | CPF |
| — | 3.2 | 1.3 | 4.5 |
| 1% (102) | 3.4 | 3.0 | 6.4 |
| 2% (102) | 4.8 | 3.1 | 7.9 |
| 1% (103) | 3.4 | 3.0 | 6.4 |
| 2% (103) | 3.4 | 4.3 | 7.7 |
| 1% (108) | 3.0 | 3.3 | 6.6 |
| 2% (108) | 3.6 | 3.6 | 7.2 |

EXAMPLE 19

Testing of alkaline earth metal salts, transition metal salts and transition metal complexes of 3-(4-methylbenzoyl)propionic acid as corrosion inhibitor in an aqueous dispersion based on an acrylic ester/styrene copolymer (Acronal S 760).

To prepare the coating composition based on Acronal S 760, the components 1 to 5 are first premixed, then the components 7 and 8 (formulation without corrosion inhibitor) or 6 to 8 (formulation with corrosion inhibitor, compound (115), Example 8) are added in the indicated order (cf. Table 9).

TABLE 9

Aqueous dispersion based on Acronal S 760

| Composition | % by weight |
|---|---|
| 1) Deionized water | 8.20 |
| 2) Pigmentverteiler NL[a] | 0.15 |
| 3) Acronal S 760 (50% grade)[b] | 8.00 |
| 4) Shellsol D 60[c] | 1.00 |
| 5) Agitan 280[d] | 0.30 |
| 6) corrosion inhibititor of the invention | — |
| 7) Millicarb[e] | 10.00 |
| 8) Bayferrox 130 M[f] | 8.00 |
| 9) Acronal S-760 (50% grade)[b] | 49.00 |
| 10) Agitan 280[d] | 0.30 |
| 11) Collacral PU 85/butyl diglycol (1:3 g/g)[g] | 4.10 |
| 12) Deionized water | 0.95 |
| Total | 100.00 |

Total solids: 57 %; a) ®Pigmentverteiler NL: dispersant (BASF AG); b) ®Acronal S 760: dispersion of an acrylic ester/styrene copolymer (aqueous dispersion, BASF AG); c) ®Shellsol D 60: white spirit (aliphatic solvent, Shell); d) ®Agitan 280: degassing and antifoam composition (Manzing Chemie GmbH); e) ®Millicarb: calcium carbonate (Omya); f) Bayferrox 130 M: iron oxide red (Bayer AG); g) ®Collacral PU 85: thickener (BASF AG).

The resulting pigment paste is dispersed with a horizontal ball mill or similar to a particle fineness <15 μm. The particle fineness is asessed by means of the grindometer value (ISO 1524).

To finish the coating, the components 9 to 12 are subsequently added in the indicated order (Table 9). Application is by conventional spraying. Depending on the viscosity desired, the finished coating can be diluted by addition of butyl diglycol/deionized water (1:1 g/g).

The coating is applied, as described in Example 17, to steel sheets of the type Bonder (cold-rolled, de-greased steel from Chemetall, Frankfurt am Main) in a thickness which is 100 μm after drying (drying conditions: 14 days at room temperature).

The salt spray test (168 hours) and the determination of the corrosion protection factors CPF are carried out as described in Example 17. The results are summarized in Table 10. The larger the numbers, the better the corrosion protection.

TABLE 10

Salt spray test, 168 hours

| Compound | CPF film | CPF metal | CPF |
|---|---|---|---|
| — | 2.4 | 2.6 | 5.0 |
| 1% (115) | 3.8 | 6.0 | 9.8 |
| 2% (115) | 4.0 | 6.0 | 10.0 |

What is claimed is:

1. An alkaline earth metal salt, transition metal salt or transition metal complex of a compound of the formula I

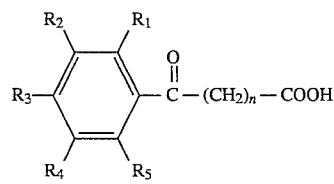

in which $R_1$, $R_2$, $R_3$, $R_4$ and $R_5$ are, independently of one another, hydrogen, halogen, nitro, cyano, $CF_3$, $C_1$–$C_{15}$alkyl, $C_5$–$C_{12}$cycloalkyl, $C_2$–$C_{15}$alkenyl, $C_1$–$C_{12}$haloalkyl, $C_1$–$C_{12}$alkoxy, $C_1$–$C_{12}$alkylthio, $C_6$–$C_{10}$aryl which is unsubstituted or substituted by $C_1$–$C_4$alkyl; $C_6$–$C_{10}$aryloxy which is unsubstituted or substituted by $C_1$–$C_4$alkyl; $C_7$–$C_{12}$arylalkyl which is unsubstituted or substituted on the aryl radical by from 1 to 3 $C_1$–$C_4$alkyl groups; —$CO_2R_6$, —$COR_6$ or

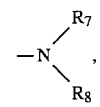

where at least one of the radicals $R_1$ to $R_5$ is hydrogen, halogen or $C_1$–$C_{15}$alkyl; or alternatively the radicals $R_1$ and $R_2$, $R_2$ and $R_3$, $R_3$ and $R_4$ or $R_4$ and $R_5$ form, together with the carbon atoms to which they are bound, a benzo or cyclohexenyl ring, $R_6$ is $C_1$–$C_{20}$alkyl, $C_2$–$C_{20}$alkyl interrupted by oxygen, sulfur or >N—$R_9$; $C_7$–$C_{12}$arylalkyl which is unsubstituted or substituted on the aryl radical by from 1 to 3 $C_1$–$C_4$alkyl groups, $R_7$ and $R_8$ are, independently of one another, hydrogen, $C_1$–$C_{24}$alkyl or $C_2$–$C_{24}$alkyl interrupted by oxygen, sulfur or >N—$R_9$, $R_9$ is hydrogen or $C_1$–$C_8$alkyl, and n is an integer in the range from 1 to 10.

2. A compound according to claim 1, in which $R_1$, $R_2$, $R_3$, $R_4$ and $R_5$ are, independently of one another, hydrogen, halogen, nitro, cyano, $CF_3$, $C_1$–$C_{15}$alkyl, $C_5$–$C_{12}$cycloalkyl, $C_2$–$C_{15}$alkenyl, $C_1$–$C_{12}$haloalkyl, $C_1$–$C_{12}$alkoxy, $C_1$–$C_{12}$alkylthio, $C_6$–$C_{10}$aryl, $C_6$–$C_{10}$aryloxy, $C_7$–$C_{12}$arylalkyl, —$CO_2R_6$, —$COR_6$ or

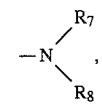

where at least one of the radicals $R_1$ to $R_5$ is hydrogen, halogen or $C_1$–$C_{15}$alkyl, in addition the radicals $R_1$ and $R_2$, $R_2$ and $R_3$, $R_3$ and $R_4$ or $R_4$ and $R_5$ form, together with the carbon atoms to which they are bound, a benzo or cyclohexenyl ring, and $R_6$ is $C_1$–$C_{20}$alkyl, $C_2$–$C_{20}$alkyl interrupted by oxygen, sulfur or >N—$R_9$; or $C_7$–$C_{12}$arylalkyl.

3. A compound according to claim 1, in which at least two of the radicals $R_1$ to $R_5$ are hydrogen.

4. A compound according to claim 1, in which the metal is calcium, titanium, manganese, iron, cobalt, zinc, yttrium, zirconium, lanthanum or cerium.

5. A compound according to claim 1, in which the metal is zirconium.

6. A compound according to claim 1, in which $R_1$ is hydrogen, $R_2$, $R_3$, $R_4$ and $R_5$ are, independently of one another, hydrogen, chlorine, bromine, nitro, cyano, $CF_3$, $C_1$–$C_8$alkyl, $C_5$–$C_7$cycloalkyl, $C_2$–$C_8$alkenyl, $C_1$–$C_8$alkoxy, $C_1$–$C_8$alkylthio, phenyl, phenyloxy, benzyl, —$CO_2R_6$, —$COR_6$ o

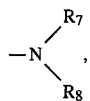

$R_6$ is $C_1$–$C_{12}$alkyl, $C_2$–$C_{12}$alkyl interrupted by oxygen; or benzyl, $R_7$ and $R_8$ are, independently of one another, hydrogen, $C_1$–$C_8$alkyl or $C_2$–$C_{12}$alkyl interrupted by oxygen, and n is an integer in the range from 1 to 5.

7. A compound according to claim 1, in which $R_1$, $R_2$ and $R_4$ are hydrogen, $R_3$ and $R_5$ are, independently of one another, hydrogen, chlorine, bromine, $CF_3$, $C_1$–$C_8$alkyl, cyclohexyl, $C_1$–$C_8$alkoxy, —$CO_2R_6$, —$COR_6$ or

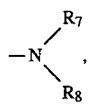

$R_6$ is $C_1$–$C_8$alkyl, $R_7$ and $R_8$ are, independently of one another, hydrogen or $C_1$–$C_8$alkyl, and n is an integer in the range from 2 to 4.

8. A compound according to claim 1, in which $R_1$, $R_2$, $R_4$ and $R_5$ are hydrogen and n is 2.

9. A compound according to claim 1, in which $R_1$, $R_2$, $R_4$ and $R_5$ are hydrogen, $R_3$ is hydrogen, $C_1$–$C_4$alkyl or chlorine, n is 2 and the metal is calcium, titanium, manganese, iron, cobalt, zinc, yttrium, zirconlure, lanthanum or cerium.

10. A coating composition comprising
   a) an organic film-forming binder and
   b) as corrosion inhibiting amount of at least one compound of the formula I according to claim 1.

11. A coating composition according to claim 10, wherein the coating composition is a liquid.

12. A coating composition according to claim 10, wherein the coating composition is a water-based liquid.

13. A coating composition according to claim 10, wherein the component a) is an epoxy resin, a polyurethane resin, a polyester resin, an acrylic resin, an acrylic copolymer resin, a polyvinyl resin, a phenolic resin, an alkyd resin or a mixture of such resins.

14. A coating composition according to claim 10, additionally comprising one or more components selected from pigments, dyes, fillers, flow modifiers, dispersants, thixotropes, adhesion promoters, antioxidants, light stabilizers or curing catalysts.

15. A coating composition according to claim 10, wherein the component b) is present in an amount from 0.01 to 20% based on the total weight of the coating composition.

16. A process for protecting a corrodable metal substrate, which comprises applying to the corrodible metal substrate a coating composition according to claim 10 and subsequently drying and optionally curing the coating.

17. A process for preparing alkaline earth metal salts, transition metal salts and transition metal complexes of compounds of the formula I according to claim 1, which comprises reacting a ketocarboxylic acid of the formula I or an alkali metal salt thereof with an alkaline earth metal or transition metal compound.

18. A process according to claim 17, wherein the alkaline earth metal or transition metal compound used is a salt, an organometallic compound or an inorganic metal base.

19. A process according to claim 17, wherein the molar ratio of the ketocarboxylic acid of the formula I to the transition metal compound is from 20:1 to 1:10.

20. A process according to claim 17, wherein the transition metal compound is a zirconium or titanium compound.

21. A product obtainable by reacting a compound of the formula I according to claim 1 or an alkali metal salt thereof with an alkaline earth metal or transition metal compound.

* * * * *